(12) United States Patent  
Geiger

(10) Patent No.: US 7,614,743 B2
(45) Date of Patent: Nov. 10, 2009

(54) VITAL SIGNS MONITORING SYSTEM WITH WIRELESS PUPILOMETER INTERFACE

(75) Inventor: Mark A. Geiger, Ventura, CA (US)

(73) Assignee: Medtronic, Inc., Minneapolis, MN (US)

( * ) Notice: Subject to any disclaimer, the term of this patent is extended or adjusted under 35 U.S.C. 154(b) by 931 days.

(21) Appl. No.: 10/976,338

(22) Filed: Oct. 28, 2004

(65) Prior Publication Data

US 2006/0030760 A1 Feb. 9, 2006

Related U.S. Application Data

(60) Provisional application No. 60/589,434, filed on Jul. 20, 2004.

(51) Int. Cl.
*A61B 3/14* (2006.01)
(52) U.S. Cl. ........................ 351/206; 351/205; 351/209; 356/214
(58) Field of Classification Search ............... 351/205, 351/206, 209; 356/214; 128/903; 340/870.07
See application file for complete search history.

(56) References Cited

U.S. PATENT DOCUMENTS

| H574 H | 2/1989 | Merkel et al. |
|---|---|---|
| 6,022,109 A | 2/2000 | Dal Santo |
| 6,199,985 B1 | 3/2001 | Anderson |
| 6,260,968 B1 * | 7/2001 | Stark et al. .................. 351/205 |
| 2002/0013518 A1 * | 1/2002 | West et al. .................. 600/300 |
| 2004/0169817 A1 | 9/2004 | Grotehusmann et al. |
| 2004/0184002 A1 | 9/2004 | Siminou et al. |

FOREIGN PATENT DOCUMENTS

WO WO 2004/058056 A1 7/2004

OTHER PUBLICATIONS

ForSite™ Pupillometer, Medtronic Neurosurgery, part of the Neurologic Technologies family of products.htm, Medtronic, Inc., 2004, 3 pgs.

* cited by examiner

*Primary Examiner*—Joseph Martinez
(74) *Attorney, Agent, or Firm*—Shumaker & Sieffert, P.A.

(57) ABSTRACT

A vital signs monitoring system and method for storing and accessing data obtained by a pupilometer make use of a pupilometer with a wireless telemetry interface to the vital signs monitor. The wireless telemetry interface permits transmission of information obtained by the pupilometer to a wireless telemetry module in a vital signs monitor. In this manner, the valuable information obtained by the pupilometer can be readily integrated with other information obtained by a vital signs monitor, and can be readily stored and retrieved by care-givers.

35 Claims, 6 Drawing Sheets

VITAL SIGNS MONITORING SYSTEM WITH WIRELESS PUPILOMETER INTERFACE

This application claims the benefit of U.S. provisional application No. 60/589,434, filed Jul. 20, 2004, the entire content of which is incorporated herein by reference.

FIELD OF THE INVENTION

The invention relates to medical devices and, more particularly, devices for monitoring physiological conditions in a patient.

BACKGROUND

Hydrocephalus is an excess buildup of cerebrospinal fluid (CSF) in the ventricles (reservoirs) of the brain, which can cause elevated intracranial pressure (ICP). Buildup occurs when the fluid cannot flow freely throughout the ventricles and the central nervous system due to various forms of blockage. Elevated ICP also may result from a brain injury or other diseases.

A pupilometer is a hand-held portable electronic instrument that assesses and records pupil size and reaction to stimulus. A pupilometer may be useful in identifying elevated ICP or other harmful brain conditions. In particular, a pupilometer may provide a rapid diagnostic tool for patients with a suspected brain injury. An example of an existing pupilometer is the Forsite™ Pupilometer, commercially available from Medtronic, Inc., of Minneapolis, Minn.

Vital signs monitors are used within a clinic or hospital, as well as in the field during delivery of emergency medical services. A vital signs monitor typically includes multiple inputs to receive vital signs information from a variety of sensors, such as electrocardiogram (ECG) electrodes, blood pressure (BP), pulse oximetry (SpO2), temperature sensors, respiration sensors, and the like.

The vital signs information is useful for real-time evaluation of the patient's conditions, as well as formulation and archival of a running record of the patient's condition over time. A pupilometer may store or output information relating to the patient's pupil state. However, pupilometer information has not been readily susceptible to integration with information obtained by a vital signs monitor, particularly in an electronic form.

U.S. Published Patent Application 20040169817 to Grotehusmann et al. describes a pupilometer for opthalmic use. U.S. Pat. No. 6,260,968 to Stark et al. describes a pupilometer for medical diagnostic use. U.S. Pat. No. 6,022,109 describes a portable, hand-held pupilometer.

Table 1 below lists documents that disclose pupilometers.

TABLE 1

| Patent Number | Inventors | Title |
| --- | --- | --- |
| 20040169817 | Grotehusmann et al. | Iris pattern recognition and alignment |
| 6,260,968 | Stark et al. | Pupilometer with pupil irregularity detection capability |
| 6,022,109 | Dal Santo | Hand-held Pupilometer |

All documents listed in Table 1 above are hereby incorporated by reference herein in their respective entireties. As those of ordinary skill in the art will appreciate readily upon reading the Summary, Detailed Description and Claims set forth below, many of the devices and methods disclosed in the patents of Table 1 may be modified advantageously by using the techniques of the present invention.

SUMMARY OF THE INVENTION

In general, the invention is directed to a vital signs monitoring system and method for storing and accessing data obtained by a pupilometer. The system includes a pupilometer with a wireless telemetry interface to the vital signs monitor. The wireless telemetry interface permits transmission of information obtained by the pupilometer to a wireless telemetry module in a vital signs monitor. In this manner, the valuable information obtained by the pupilometer can be readily integrated with other information obtained by a vital signs monitor, and can be readily stored and retrieved by care-givers.

Various embodiments of the present invention provide solutions to one or more problems existing in the prior art with respect to prior art systems for monitoring vital signs. These problems include the inability to readily integrate pupilometer information with other vital signs information for real-time evaluation or archival of the state of a patient over a period of time. Although pupilometer information can be very important in evaluating the condition of a patient, particularly following a brain injury, the inability to readily integrate pupilometer information with other vital signs information can undermine the prominence of such information as part of a patient record. Rather than being incorporated in a patient record with other vital signs, the pupilometer information is typically recorded and stored separately, e.g., as a printout. Moreover, the pupilometer information is not displayed along with other vital signs information consulted by a care-giver in the course of delivering clinical, hospital or emergency medical services. Instead, the pupilometer includes its own display, which is viewed separately from other vital sign information.

Various embodiments of the present invention are capable of solving at least one of the foregoing problems. When embodied in a system or method for monitoring vital signs, the invention includes features that facilitate the ready integration of pupilometer information with other vital signs information for real-time evaluation or record-keeping purposes. In this manner, the invention can enhance the prominence of pupilometer information among other vital signs information consulted by a care-giver, promoting more effective diagnosis of brain injury or excessive intra-cranial pressure. The invention provides a wireless telemetry interface between a vital signs monitor and a pupilometer. The pupilometer may be a portable, handheld pupilometer. The vital signs monitor may be a bedside or portable vital signs monitor. In some embodiments, a pupilometer may communicate with multiple vital signs monitors. Also, the pupilometer information may be accessible via a network. The wireless telemetry interface may support radio frequency (RF) or infrared (IR) communication.

In one embodiment, the invention provides a vital signs monitoring system comprising a pupilometer to obtain pupilometer information, the pupilometer including a first wireless telemetry module to transmit the information, a vital signs monitor having a second wireless telemetry module to receive the transmitted information.

In another embodiment, the invention provides a method for monitoring vital signs, the method comprising obtaining pupilometer information at a pupilometer, transmitting the pupilometer information from the pupilometer to a vital signs monitor via a wireless telemetry module, and presenting the pupilometer information via a display associated with the vital signs monitor.

In a further embodiment, the invention provides a pupilometer comprising an illumination unit to stimulate a pupil of a patient, a camera to obtain one or more images indicating a reaction of the pupil, a processor to process the images and generate pupilometer information, and a wireless telemetry module to transmit the pupilometer information to a vital signs monitor via a wireless telemetry module.

In comparison to known techniques for monitoring vital signs, various embodiments of the invention may provide one or more advantages. For example, the invention facilitates the integration of pupilometer information with other vital signs information for quick, convenient viewing and consideration by a care-giver. In addition, the invention facilitates integrated record-keeping that incorporates pupilometer information with other vital signs information for archival and subsequent evaluation. The valuable information provided by a pupilometer is more likely to be considered prominently among other vital signs when making care decisions or diagnoses, whether in a clinical, hospital or emergency setting. In this manner, the invention can promote evaluation of a more comprehensive set of vital signs information, which may contribute to improved patient care, especially for patients suffering a brain injury.

The details of one or more embodiments of the invention are set forth in the accompanying drawings and the description below. Other features, objects, and advantages of the invention will be apparent from the description and drawings, and from the claims.

DESCRIPTION OF THE PREFERRED EMBODIMENTS

Figure 1:
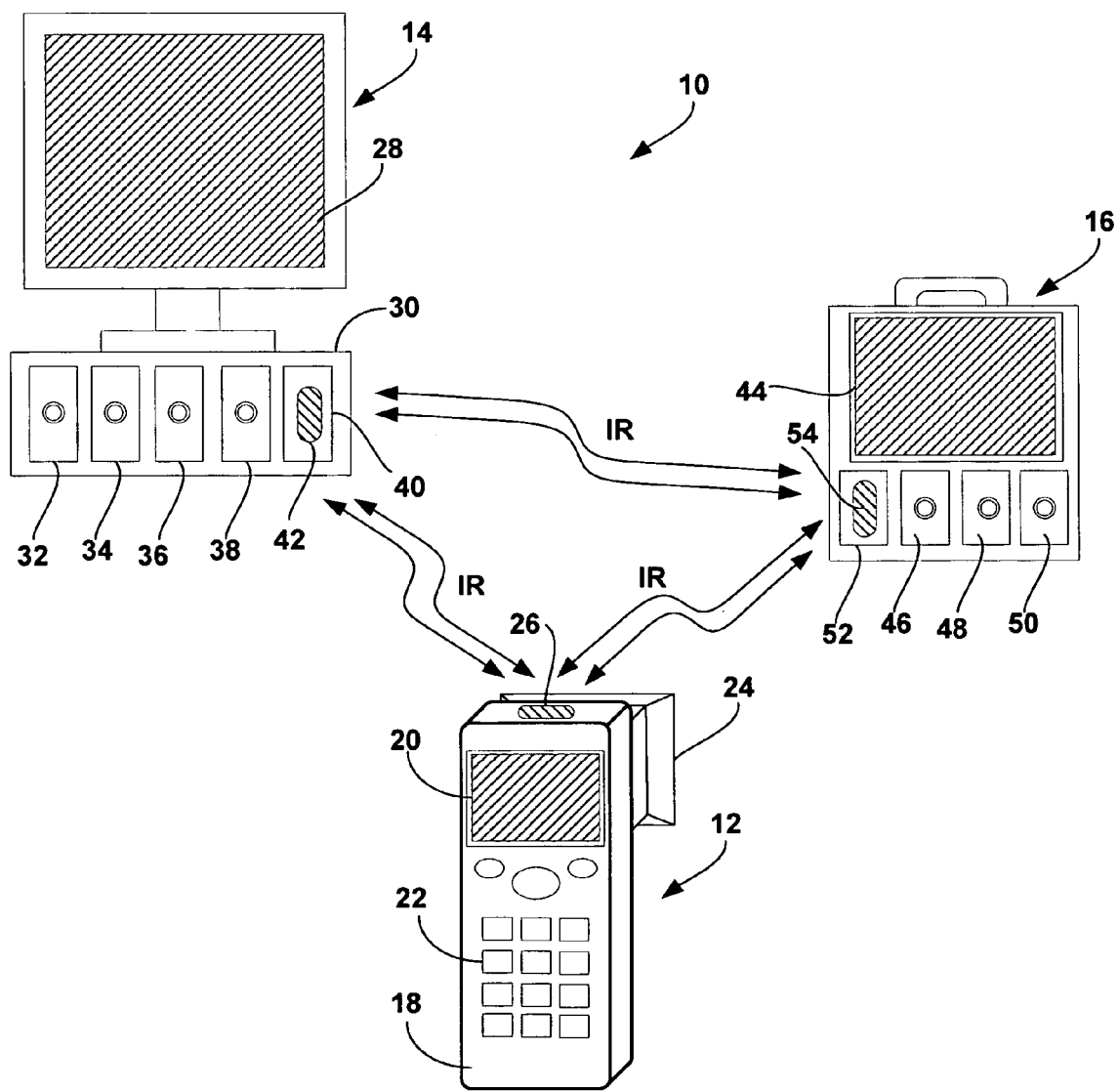
FIG. 1 is a schematic diagram illustrating a vital signs monitoring system providing an infrared telemetry interface with a pupilometer.

FIG. 1 is a schematic diagram illustrating a vital signs monitoring system 10 for obtaining, storing and accessing data obtained by a pupilometer 12. As shown in FIG. 1, system 10 may include pupilometer 12 and one or more vital signs monitors 14, 16. Vital signs monitor 14 may be used in a clinical or hospital setting, e.g., as a bedside or operating room monitor. Vital signs monitor 16 is portable, and may be used with ambulatory patients within a clinic or hospital, or with patients in the field during delivery of emergency medical services.

In accordance with the invention, pupilometer 12 and vital signs monitors 14, 16 include a wireless telemetry interface that permits transmission of pupilometer information to the vital signs monitors for display and storage with other vital signs information. For example, pupilometer 12 may transmit information to vital signs monitor 14, vital signs monitor 16, or both. In some embodiments, vitals signs monitors 14, 16 may exchange information with one another. Also, pupilometer 12 may be equipped to receive information from one or both of vital signs monitors 14, 16.

In the example of FIG. 1, pupilometer 12 is a portable, handheld device equipped for infrared communication. To that end, pupilometer includes an infrared transceiver 26. Pupilometer 12 may include a housing 18 with a display and a set of user input media, such as buttons 22. An eye cup 24 extends from pupilometer 12 for application to a patient's eye. In operation, pupilometer 12 emits a burst of light to stimulate the patient's pupil. A camera within pupilometer 12 captures one or more images of the pupil during stimulation. Pupilometer 12 then processes the images to generate pupilometer information characterizing pupil response such as pupil dynamics. The pupilometer information may provide an indication of brain injury, including increased intracranial pressure or other conditions. The pupilometer information transmitted by pupilometer 12 also may include information relating to patient identification, date, time, and the like.

Bedside vital signs monitor 14 includes a display 28 and a chassis 30 containing appropriate electronics to process vital signs inputs and drive the display to present information based on the inputs. For example, chassis 30 may serve as a rack to contain multiple vital signs modules 32, 34, 36, 38 designed to receive vital signs information from various sensors. The number of modules may vary. In addition, in some embodiments, different modules may be swapped in and out of chassis 30 according to the needs or specifications of particular care-givers. Notably, bedside vital signs monitor 14 further includes a wireless telemetry module 40 equipped to communicate with pupilometer. In the example of FIG. 1, wireless telemetry module 40 includes an infrared transceiver 42.

Portable vital signs monitor 16 includes a display 44 and various vital signs modules 46, 48, 50 to receive vital signs information modules from various sensors. Like bedside vital signs monitor 14, portable vital signs monitor 16 may permit different modules to be swapped in and out of respective module bays in the monitor chassis. Portable vital signs monitor 14 also includes a wireless telemetry module 52 with an infrared transceiver 54. Wireless telemetry module 52 is equipped to receive pupilometer information from pupilometer 12. In pupilometer 12 and vital signs monitors 14, 16, the infrared interface may conform to a standard protocol, such as the IrDA protocol promulgated by the Infrared Data Association.

With the availability of a wireless telemetry link between pupilometer 12 and vital signs monitors 14, 16, pupilometer information can be displayed with other vital signs information on displays 28, 44. In addition, the pupilometer information can be recorded and archived as part of a patient record with other vital signs information. In some embodiments, the wireless transmission of pupilometer information can be made in response to a command by a user of pupilometer 12. For example, a user may use pupilometer 12 to gather information from the patient and then transmit the information to one of vital signs monitors 14, 16. Alternatively, a user may select one or more patient records archived within a memory associated with pupilometer, and then selectively transmit pupilometer information contained in the patient records as desired. For example, pupilometer 12 may be equipped to store hundreds of patient records containing pupilometer information. As a further alternative, pupilometer 12 may be configured to automatically transmit information to one of vital signs monitors 14, 16 upon acquisition of pupilometer information from a patient.

Upon receipt of the pupilometer information, a vital signs monitor 14, 16 may present all of some of the information via a respective display 28, 44. The information may be displayed with other vital signs information, or displayed independently. In some embodiments, a user may enter input to cause a vital signs monitor 14, 16 to selectively display pupilometer information as desired. In addition, a vital signs monitor 14, 16 may record the pupilometer information in a patient record with other vital signs information. In each case, the wireless information promotes ready integration of the pupilometer information with other vital signs information. Consequently, the valuable information provided by pupilometer 12 is featured more prominently among the vital signs considered by a care-giver when making a care decision or diagnosis.

In some embodiments, one or both of vital signs monitors 14, 16 may be connected to a network (not shown), such as a local area network or wide area network serving a clinic, hospital or emergency response network. Accordingly, information obtained from pupilometer 12 may be transferred from vital signs monitors 14, 16 to other archival, presentation or analysis systems used by care-givers. In this manner, with the aid of the wireless telemetry interface, a care-giver may obtain remote access to pupilometer information and render care decisions or diagnoses on a remote basis. In addition, the pupilometer information can be archived to a central recordkeeping system via a network connection.

Figure 2:
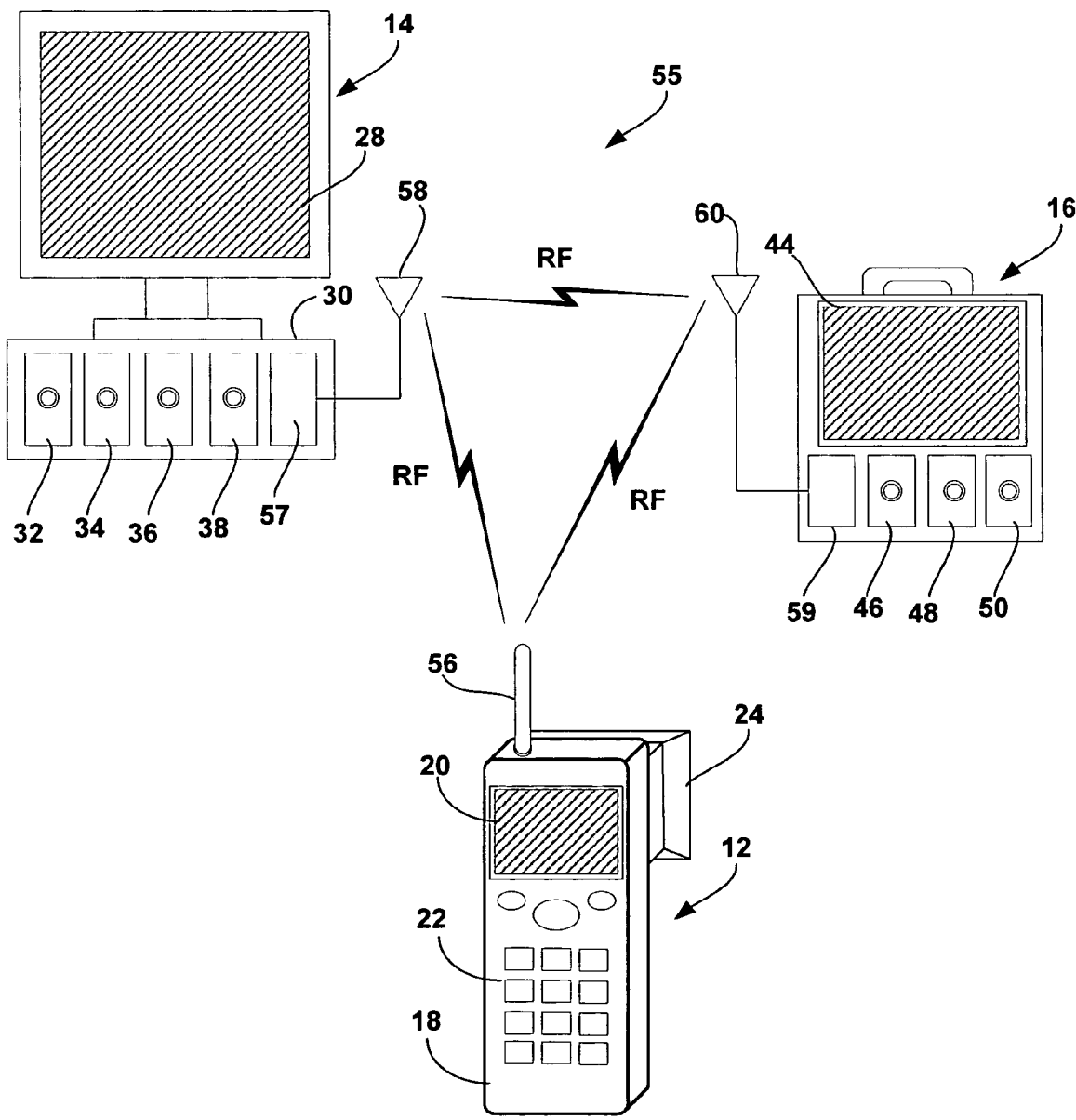
FIG. 2 is a schematic diagram illustrating a vital signs monitoring system providing a radio frequency telemetry interface with a pupilometer.

FIG. 2 is a schematic diagram illustrating a vital signs monitoring system 55 providing a radio frequency (RF) telemetry interface to support an RF communication link with pupilometer 12. System 55 corresponds substantially to system 10 of FIG. 1, but depicts the use of an RF telemetry interface between pupilometer 12 and vital signs monitors 14, 16. In particular, instead of an infrared transceiver, pupilometer 12 includes an RF transceiver and an antenna 56. Similarly, vital signs monitor 14 includes an RF module 57 with an RF antenna 58, and vital signs monitor 16 includes an RF module 59 with an RF antenna 60.

In the example of FIG. 2, pupilometer 12 and vital signs monitors 14, 16 communicate with one another by wireless communication directly with one another. Pupilometer 12 and vital signs monitors 14, 16 may be equipped for direct wireless communication according to any of a variety of protocols or standards. As one example, pupilometer 12 and vital signs monitors 14, 16 may be configured to communicate according to the Bluetooth standards promulgate by the Bluetooth Special Interest Group (SIG). Alternatively, pupilometer 12 and vital signs monitors 14, 16 may communicate according to any of the various IEEE 802.11 wireless networking protocols, such as 802.11a, 802.11b, 802.11e or 802.11g.

Figure 3:
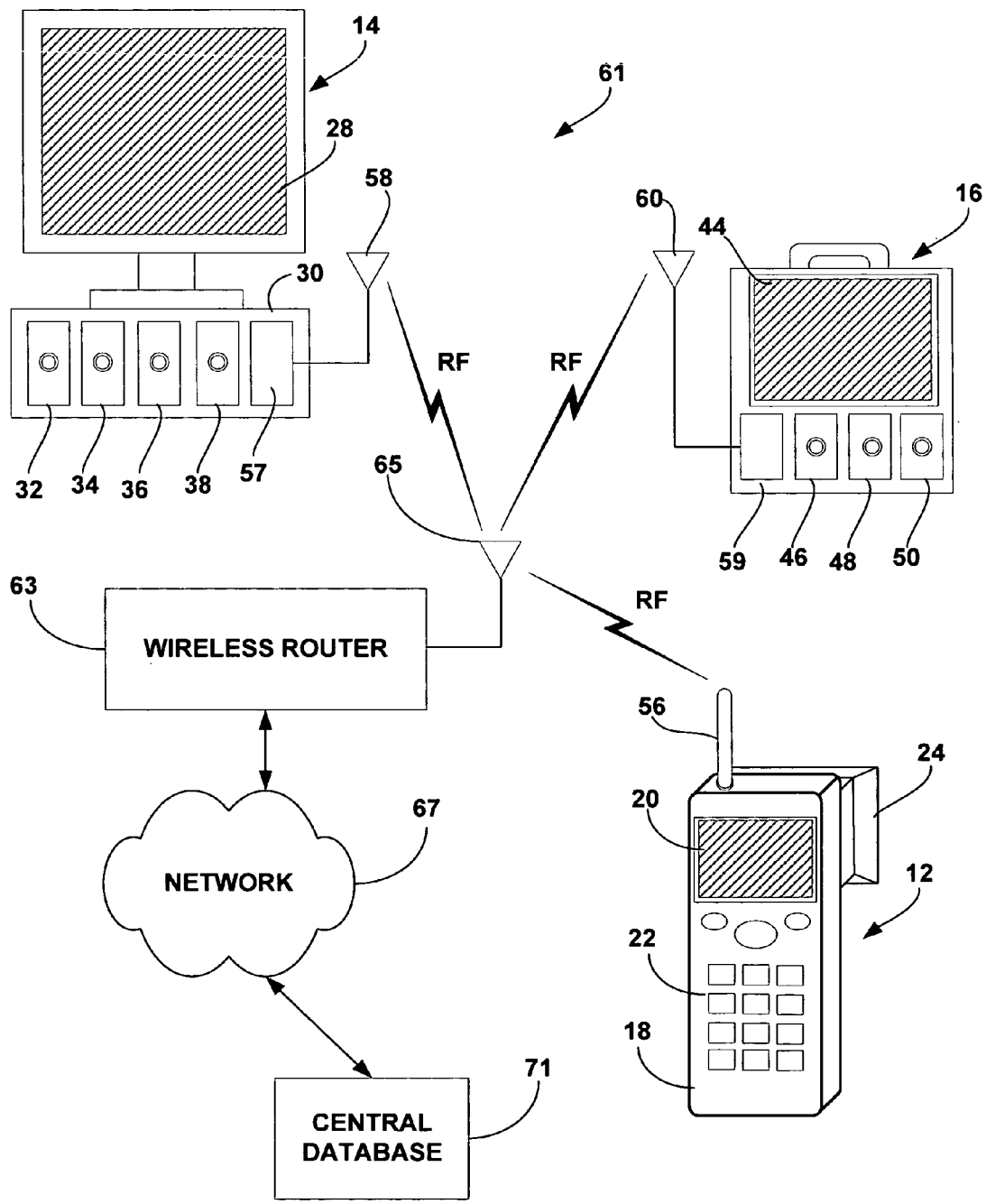
FIG. 3 is a schematic diagram illustrating a vital signs monitoring system providing a radio frequency networked telemetry interface with a pupilometer.

FIG. 3 is a schematic diagram illustrating a vital signs monitoring system 61 providing an RF networked telemetry interface with a pupilometer 12. System 61 conforms substantially to system 55 of FIG. 2, but illustrates a networked configuration in which respective wireless transceivers associated with pupilometer 12 and vital signs monitors 14, 16 communicate via a wireless router 63 having an RF antenna 65. Wireless router 63 transfers packets between pupilometer 12 and vital signs monitors 14, 16, and may provide access to a larger network 67, such as a local area network or wide area network serving a clinic, hospital or emergency response network. For example, pupilometer information may be uploaded to a central database 71 for recordkeeping and retrieval by caregivers for remote presentation and analysis.

Figure 4:
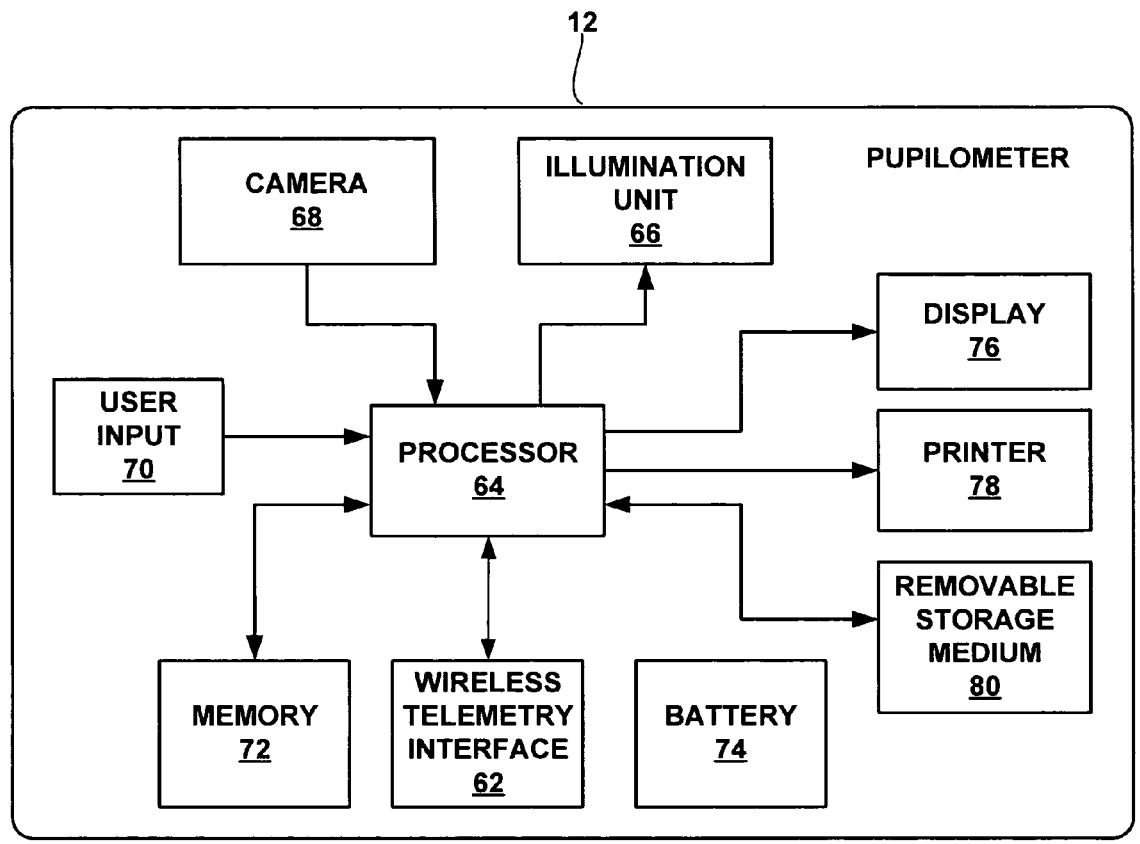
FIG. 4 is a functional block diagram of a pupilometer with a wireless telemetry interface.

FIG. 4 is a functional block diagram of a pupilometer 12 with a wireless telemetry interface as described herein. Pupilometer 12 may conform substantially to the Forsite Pupilometer commercially available from Medtronic, Inc. of Minneapolis, Minn. In accordance with the invention, pupilometer 12 is further equipped with a wireless telemetry interface 62. As shown in FIG. 4, pupilometer 12 may include a processor 64, illumination unit 66, camera 68, user input device 70, memory 72, battery 74, and display 76. In addition, pupilometer 12 optionally may include a printer 78 and an interface for a removable storage medium 80. Battery 74 provides power to pupilometer 12, and may be rechargeable.

User input device 70 may include a variety of different input media such as buttons, keys, dials, switches, and the like. Display 76 may be any of a variety of different display devices, such as liquid crystal display (LCD), plasma display, or the like. In some embodiments, user input device 70 may include soft keys displayed by display 76 and selected using buttons carried by pupilometer 12. Display 76 also presents pupilometer information to a user for use in evaluation of a patient. For example, display 76 may present the pupilometer information by graphical representation, textual representation, or both.

In operation, illumination unit 66 generates illumination to stimulate the pupil of a patient to elicit a dynamic pupil response. Illumination unit 66 includes a light source to stimulate a patient's pupil response. Camera 68 captures a series of images of the pupil's response to the light stimulus. Processor 64 applies an image processing routine to the images to produce pupilometer information, such as pupilary size, latency, construction, and dilation velocities. In this way, processor 64 can provide an indication of whether the patient's pupil is reacting abnormally, which may indicate brain trauma, elevated ICP, or other disorders. Evaluation of the size, light reactivity and equality of the pupils can be an important part of patient evaluation following an injury or surgery, in terms of identifying neurological disorders.

The structure and operation of pupilometer 12 for obtaining pupilometer information may be similar to conventional pupilometer devices. The pupilometer information can be stored in memory 72, presented to the user via display 76, and printed via printer 78, if desired. In addition, the information can be stored on removable media, such as a solid state memory card, for use by other devices. Processor 64 can create multiple patient records containing pupilometer information for different patients or both eyes of a patient. In some embodiments, printer 78 may be linked to pupilometer 12 via an infrared or RF link to transmit information for printout.

A user can instruct processor 64 to select particular patient records via user input device 70, and transmit the records to a vital signs monitor 14, 16 via wireless telemetry interface 62. As discussed with reference to FIGS. 1-3, wireless telemetry interface 62 may operate using infrared or RF telemetry. In each case, to transmit a patient record, wireless telemetry interface 62 first establishes a network relationship with one or more vital signs monitors 14, 16. The relationship may be peer-to-peer, master-slave, or client-server.

Figure 5:
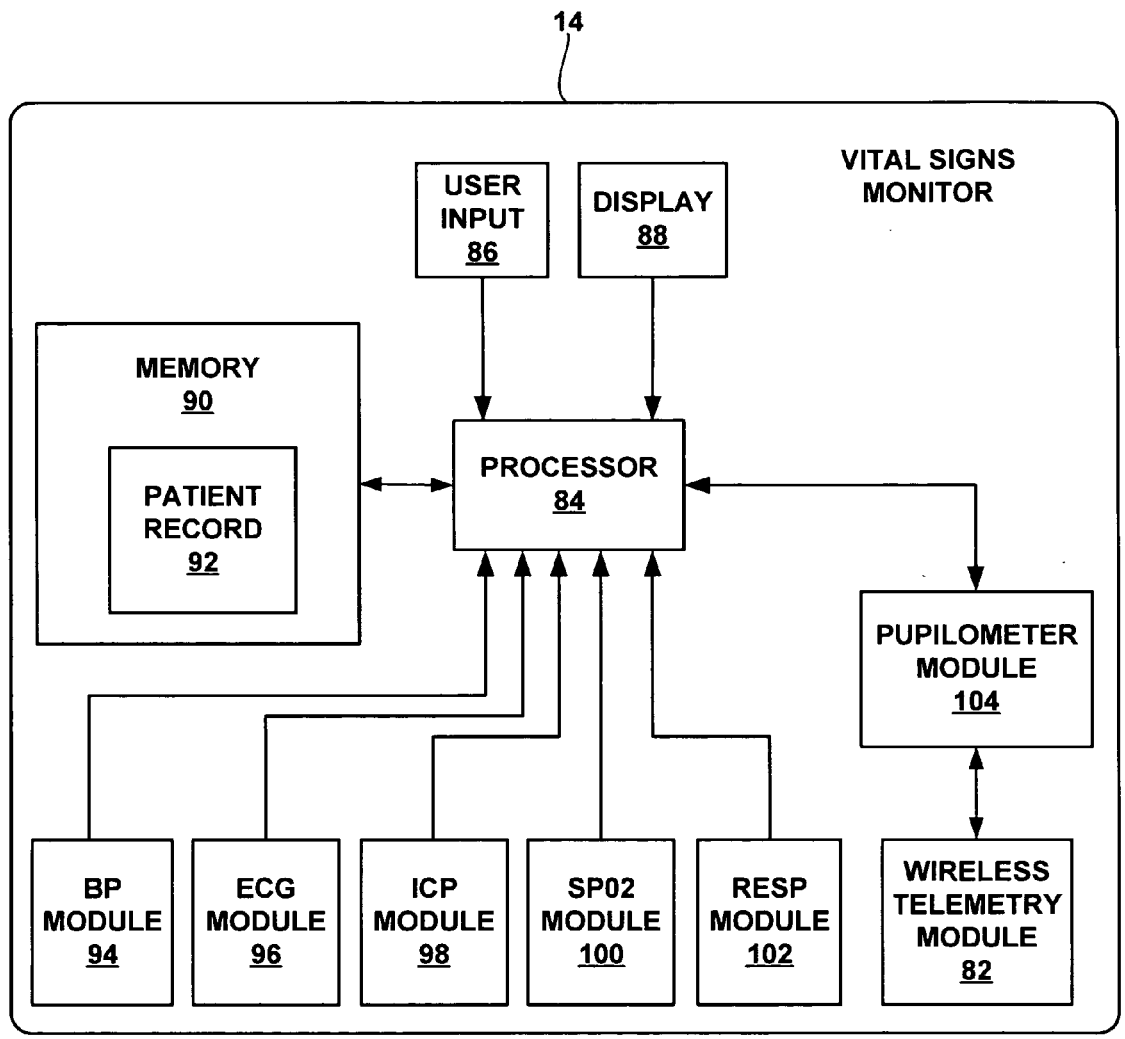
FIG. 5 is a functional block diagram of a vital signs monitor with a wireless telemetry interface.

FIG. 5 is a functional block diagram of a vital signs monitor 14 with a wireless telemetry interface 82. In the example of FIG. 5, vital signs monitor 14 is depicted as a bedside monitor, although similar components may be provided in a portable monitor such as monitor 16 of FIGS. 1-3. As shown in FIG. 5, vital signs monitor 14 includes a processor 84, user input device 86, display 88, and a memory 90. Memory 90 may store program instructions for execution by processor 84, and archive vital signs information, e.g., in an electronic patient record 92. In addition, vital signs monitor 14 includes multiple vital signs modules. Each vital signs module provides appropriate electronic circuitry to interface with a vital signs sensor. For example, a given module may include appropriate amplifier, filtering, signal processing and digital-to-analog conversion circuitry, and presents digital vital signs information to processor 84 for further processing, presentation and storage.

As examples, vital signs monitor 14 may include a blood pressure (BP) module 94, electrocardiogram (ECG) module 96, intracranial pressure (ICP) module 98, pulse oximetry (SpO2) module 100, and respiration unit 102. Modules 94-102 may receive physical cables provided from appropriate sensors or sensing devices. Alternatively, vital signs monitor 14 may provide one or more wireless interfaces to such sensors or sensing devices. In addition, in accordance with the invention, vital signs monitor 14 includes a pupilometer module 104 and a wireless telemetry interface 106 to receive pupilometer information from pupilometer 12. Wireless telemetry interface 106 may be an infrared or RF interface, and may fit into an existing chassis or module rack associated with a vital signs monitor.

User input device 86 may take a variety of forms, including buttons, keys, dials, switches, or a full keyboard and point device, which permit a user to access and display different vital signs information on a selective basis. In some embodiments, a user may configure preferences or display templates to organize information, including pupilometer information, for presentation on display 88, which may be an LCD, plasma display, or cathode ray tube (CRT) or the like.

Pupilometer module 104 processes the pupilometer information received via wireless telemetry interface 82 for integration with other vital signs information obtained via modules 94-102. For example, processor 84 may present pupilometer information with other vital signs information on display 88, or integrate the pupilometer information with other vital signs information in a patient record 92 in memory 90.

In some embodiments, pupilometer module 104 or processor 84 may provide additional processing of pupilometer information. For example, a vital signs monitor 14, 16 may be set to emit a visual or audible alarm at programmed levels and show data trends over time. Hence, vital signs monitor 14, 16 may provide alarms that are responsive to different levels expressed by the pupilometer information, and may generate trend data illustrating changes in the pupilometer information over time.

In this manner, the information obtained by the pupilometer can be readily integrated with other information obtained by a vital signs monitor 14, and can be readily stored and retrieved by care-givers. Transmission of pupilometer information from pupilometer facilitates the integration of pupilometer information with other vital signs information for quick, convenient viewing and consideration by a care-giver. In addition, vital signs monitor 14 can facilitate integrated record-keeping that incorporates pupilometer information with other vital signs information in a patient record 92 for archival and subsequent evaluation.

Figure 6:
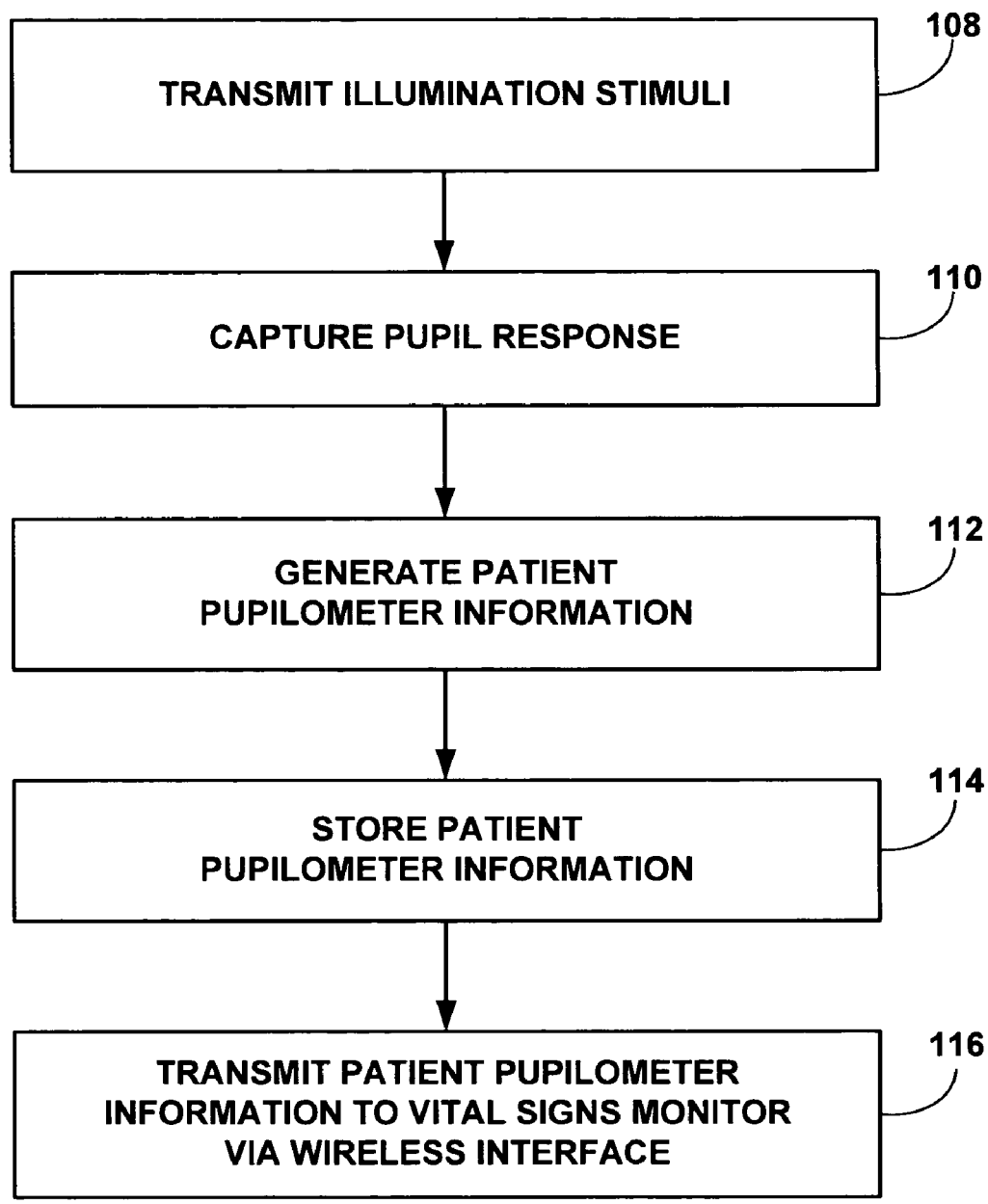
FIG. 6 is a flow diagram illustrating a technique for exchanging information between a vital signs monitor and a pupilometer via a wireless telemetry interface.

FIG. 6 is a flow diagram illustrating a technique for exchanging information between a vital signs monitor 14 and a pupilometer 12 via a wireless telemetry interface. As shown in FIG. 6, pupilometer 12 transmits illumination stimuli to stimulate a pupil response in the patient (108), captures the response with a camera (110), and generates patient pupilometer information (112). Upon storing the patient pupilometer information in local memory on the pupilometer 12 (114), the pupilometer transmits the pupilometer information to a vital signs monitor via a wireless interface (116). The pupilometer information may be transmitted immediately upon acquisition, or transmitted selectively in response to user input.

In some embodiments, pupilometer 12 also may be configured to receive information from a vital signs monitor 14, 16 via a wireless interface. If a vital signs monitor is a master in a master-slave relationship, for example, the vital signs monitor may assign time slots or frequency channels to pupilometer 12 to avoid collision of transmissions from other devices. In addition, in a master-slave, peer-to-peer or client-server relationship, pupilometer 12 and vital signs monitor 14, 16 may exchange information concerning required transmit strength, necessary retries, error correction and other functions. Also, pupilometer 12 may be configured to receive information from vital signs monitor 14, 16 for inclusion in the pupilometer information, such as patient identification, care-giver identification, date, time, or the like. Bi-directional communication between pupilometer 12 and vital signs monitor 14, 16 ordinarily will be desirable. Accordingly, the respective wireless telemetry modules within pupilometer 12 and vital signs monitors 14, 16 may include both transmitters and receivers.

There are many different types of monitoring devices for critically ill patients in the intensive care unit (ICU) and emergency room (ER). Many of these monitoring devices do not effectively communicate with each other or a network within a clinic, hospital or emergency services organization. One established conduit to such a network is the bedside vital signs monitor.

In accordance with the invention, pupilometer 12 is equipped with a wireless telemetry module, e.g., RF or infrared, to upload patient measurements to a bedside vital signs monitor in the hospital or a mobile vital signs monitor in the field with a paramedic. The pupilometer then may communicate with the vital signs monitor for display and correlations of the uploaded information with other patient parameters, and for storage, e.g., on a clinic, hospital or emergency medical services network. Consequently, a paper record from the pupilometer printer would only be needed as a backup to the information stored on the network.

A processor, as described herein, e.g., within pupilometer 12 or vital signs monitors 14, 16, may be implemented as one or more microprocessors, microcontrollers, digital signal processors, application specific integrated circuits (ASICs), field programmable logic arrays (FPGAs), or other equivalent integrated or discrete logic circuitry. Various aspects of the techniques described herein may be implemented in hardware, software, firmware, or any combination thereof. If implemented in software, the techniques may be embodied as instructions on a computer-readable medium such as random access memory (RAM), read-only memory (ROM), non-volatile random access memory (NVRAM), electrically erasable programmable read-only memory (EEPROM), FLASH memory, or the like. The instructions may cause one or more processors to perform certain aspects of the functionality described in this disclosure.

The preceding specific embodiments are illustrative of the practice of the invention. It is to be understood, therefore, that other expedients known to those skilled in the art or disclosed herein may be employed without departing from the invention or the scope of the claims.

For example, the invention is not limited to monitoring brain injury or elevated ICP. In addition to assessing brain trauma of elevated ICP, pupilometer 12 may be useful in identifying other neurological disorders, strokes, Alzheimer's disease, intoxication or drug use. Accordingly, a pupilometer 12 with a wireless interface to a vital signs monitor provides an opportunity to upload a wealth of information that may be useful in a variety of settings.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A vital signs monitoring system comprising:
   a pupilometer to obtain pupilometer information from a patient, the pupilometer including a first wireless telemetry module to transmit the information; and
   a vital signs monitor that is associated with the patent and not associated with any other patients having a second wireless telemetry module to receive the transmitted information.

2. The system of claim 1, wherein each of the wireless telemetry modules includes an infrared telemetry module.

3. The system of claim 1, wherein the infrared telemetry module operates according to an IrDA protocol.

4. The system of claim 1, wherein each of the wireless telemetry modules includes a radio frequency (RF) telemetry module;

5. The system of claim 4, wherein the RF telemetry module operates according to one of the IEEE 802.11 protocols and a Bluetooth protocol.

6. The system of claim 1, wherein the pupilometer information includes pupil dynamic information.

7. The system of claim 6, wherein the pupilometer information includes patient identification, date and time.

8. The system of claim 1, wherein the first telemetry module includes a transmitter to transmit the pupilometer information and a receiver to receive information from the vital signs monitor.

9. The system of claim 1, wherein the pupilometer is a handheld, battery-powered device.

10. The system of claim 1, wherein the pupilometer includes a display and a user input device to select one or more patient records containing the pupilometer information for transmission to the vital signs monitor.

11. The system of claim 1, wherein the vital signs monitor includes a display and a processor to drive the display to present the pupilometer information with other vital signs information.

12. The system of claim 1, wherein the vital signs monitor includes multiple vital signs modules to receive vital signs information.

13. The system of claim 12, wherein the vital signs information includes blood pressure information, pulse oximetry information, and electrocardiogram information.

14. The system of claim 1, wherein the vital signs monitor is a portable vital signs monitor.

15. The system of claim 1, wherein the vital signs monitor is selected from a group consisting of:
   a bedside monitor; and
   a portable monitor.

16. A method for monitoring vital signs of a patient, the method comprising:
   obtaining pupilometer information from the patient at a pupilometer;
   transmitting the pupilometer information from the pupilometer to a vital signs monitor that is associated with the patent and not associated with any other patients via a wireless telemetry module; and
   presenting the pupilometer information via a display associated with the vital signs monitor.

17. The method of claim 16, further comprising transmitting the pupilometer information via an infrared telemetry module.

18. The method of claim 17, wherein the infrared telemetry module operates according to an IrDA protocol.

19. The method of claim 16, further comprising transmitting the pupilometer information via a radio frequency (RF) telemetry module.

20. The method of claim 19, wherein the RF telemetry module operates according to one of the IEEE 802.11 protocols and a Bluetooth protocol.

21. The method of claim 16, wherein the pupilometer information includes pupil dynamic information.

22. The method of claim 16, wherein the pupilometer information includes patient identification, date and time.

23. The method of claim 16, further comprising receiving information at the pupilometer from the vital signs monitor via the wireless telemetry module.

24. The method of claim 16, further comprising selecting one or more patient records containing the pupilometer information for transmission to the vital signs monitor in response to user input.

25. The method of claim 16, further comprising driving a display associated with the vital signs monitor to present the pupilometer information with other vital signs information.

26. The method of claim 25, wherein the other vital signs information includes blood pressure information, pulse oximetry information, and electrocardiogram information.

27. A pupilometer comprising:
   an illumination unit to stimulate a pupil of a patient;
   a camera to obtain one or more images indicating a reaction of the pupil;
   a processor to process the images and generate pupilometer information; and
   a wireless telemetry module to transmit the pupilometer information to a vital signs monitor that is associated with the patent and not associated with any other patients via a wireless telemetry module.

28. The pupilometer of claim 27, wherein the wireless telemetry module includes an infrared telemetry module.

29. The pupilometer of claim 27, wherein the infrared telemetry module operates according to an IrDA protocol.

30. The pupilometer of claim 27, wherein the wireless telemetry module includes a radio frequency (RF) telemetry module.

31. The pupilometer of claim 30, wherein the RF telemetry module operates according to one of the IEEE 802.11 protocols and a Bluetooth protocol.

32. The pupilometer of claim 27, wherein the pupilometer information includes pupil dynamic information and patient identification, date and time.

33. The pupilometer of claim 27, wherein the telemetry module includes a transmitter to transmit the pupilometer information and a receiver to receive information from the vital signs monitor.

34. The pupilometer of claim 27, wherein the pupilometer is a handheld, battery-powered device.

35. The pupilometer of claim 27, wherein the pupilometer includes a display and a user input device to select one or more patient records containing the pupilometer information for transmission to the vital signs monitor.

* * * * *

UNITED STATES PATENT AND TRADEMARK OFFICE
CERTIFICATE OF CORRECTION

PATENT NO. : 7,614,743 B2  Page 1 of 1
APPLICATION NO. : 10/976338
DATED : November 10, 2009
INVENTOR(S) : Mark A. Geiger It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 984 days.

Signed and Sealed this

Nineteenth Day of October, 2010

David J. Kappos
*Director of the United States Patent and Trademark Office*